US00PP11511P

United States Patent [19]

Kudo

[11] Patent Number: Plant 11,511

[45] Date of Patent: Sep. 19, 2000

[54] APPLE TREE VARIETY NAMED 'MIKI LIFE'

[76] Inventor: Seiichi Kudo, 15, Aza Harusinai, Ooaza Ishikawa, Hirosaki City, Aomori, Japan

[21] Appl. No.: 08/744,875

[22] Filed: Nov. 8, 1996

[51] Int. Cl.[7] ..... A01H 5/00

[52] U.S. Cl. ..... Plt./161

[58] Field of Search ..... Plt./34.1, 161, Plt./168

*Primary Examiner*—Howard J. Locker

*Attorney, Agent, or Firm*—Armstrong, Westerman, Hattori, McLeland & Naughton

[57] ABSTRACT

An apple tree variety bearing early maturing fruit easily coloring in warm weather, having a greenish ground color and bright red overcolor with red stripes, and having a coarse flesh which is very juicy, moderately sweet and with low acidity.

6 Drawing Sheets

The present invention relates to a new and distinct variety of apple tree for a dessert apple, which is an early apple cultivar easily coloring in hot weather.

This new and distinct cultivar was bred by Seiichi Kudo who crossed 'SENSHU' with 'TSUGARU' in 1981. The following spring he seeded one hundred seeds of the cross and developed one hundred seedlings in his orchard (at No. 63, aza Izumida, Ooaza Ishikawa, Hirosaki City, Aomori prefecture, Japan). In 1988 he gathered the first crop from the seedlings. He selected one tree with brilliant red fruit ripening early in the season. For confirmation of the stability of the characteristics of the seedling, he grafted the bud-woods on other trees in 1989 at the same orchard. Continued observation of the seedlings indicated that the characteristics of the variety of the invention are stable, and are transmitted without change through succeeding propagation.

'MIKI LIFE' is an early ripening cultivar, ripening about three to four weeks earlier than 'KANKI' which is an intermediate ripening variety also developed by Seiichi Kudo by crossing 'SENSHU' with 'TSUGARU', as described in U.S. plant patent application Ser. No. 08/747,284, filed Nov. 12, 1996. 'TSUGARU' is the only widely cultivated early variety which ripens in the same season as 'MIKI LIFE'.

BRIEF DESCRIPTION OF THE DRAWINGS

The accompanying photographic illustrations show typical specimens of the foliage and fruit of the new variety. The colors depicted are as true as is reasonably possible to attain in color illustrations of this character.

DETAILED DESCRIPTION OF VARIETY

Figure 1:
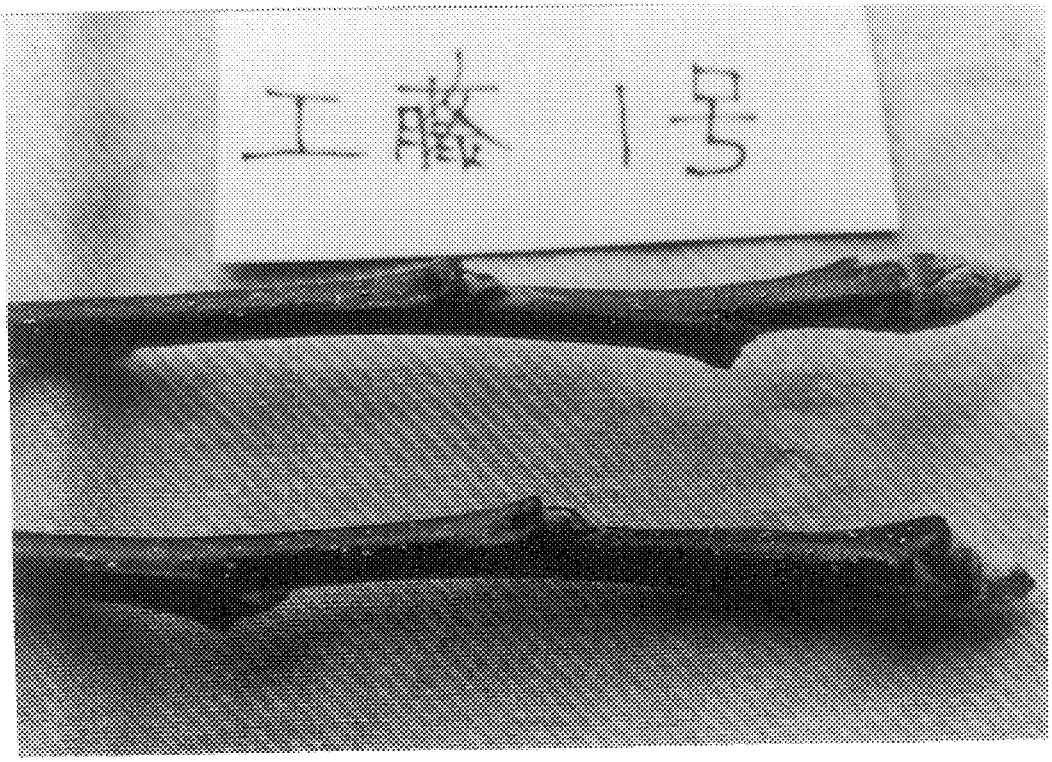
FIG. 1 is a photograph illustrating buds, stem coloration, and lenticels.
Figure 2:
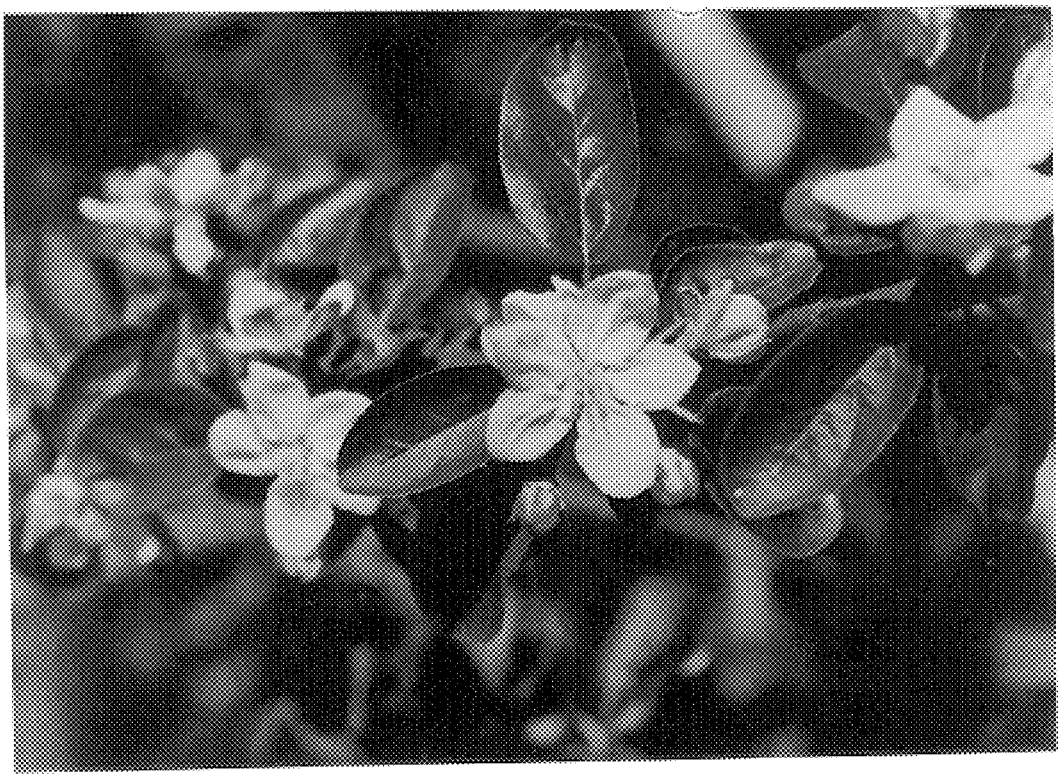
FIG. 2 is a photograph showing buds, open blooms, and foliage.
Figure 3:
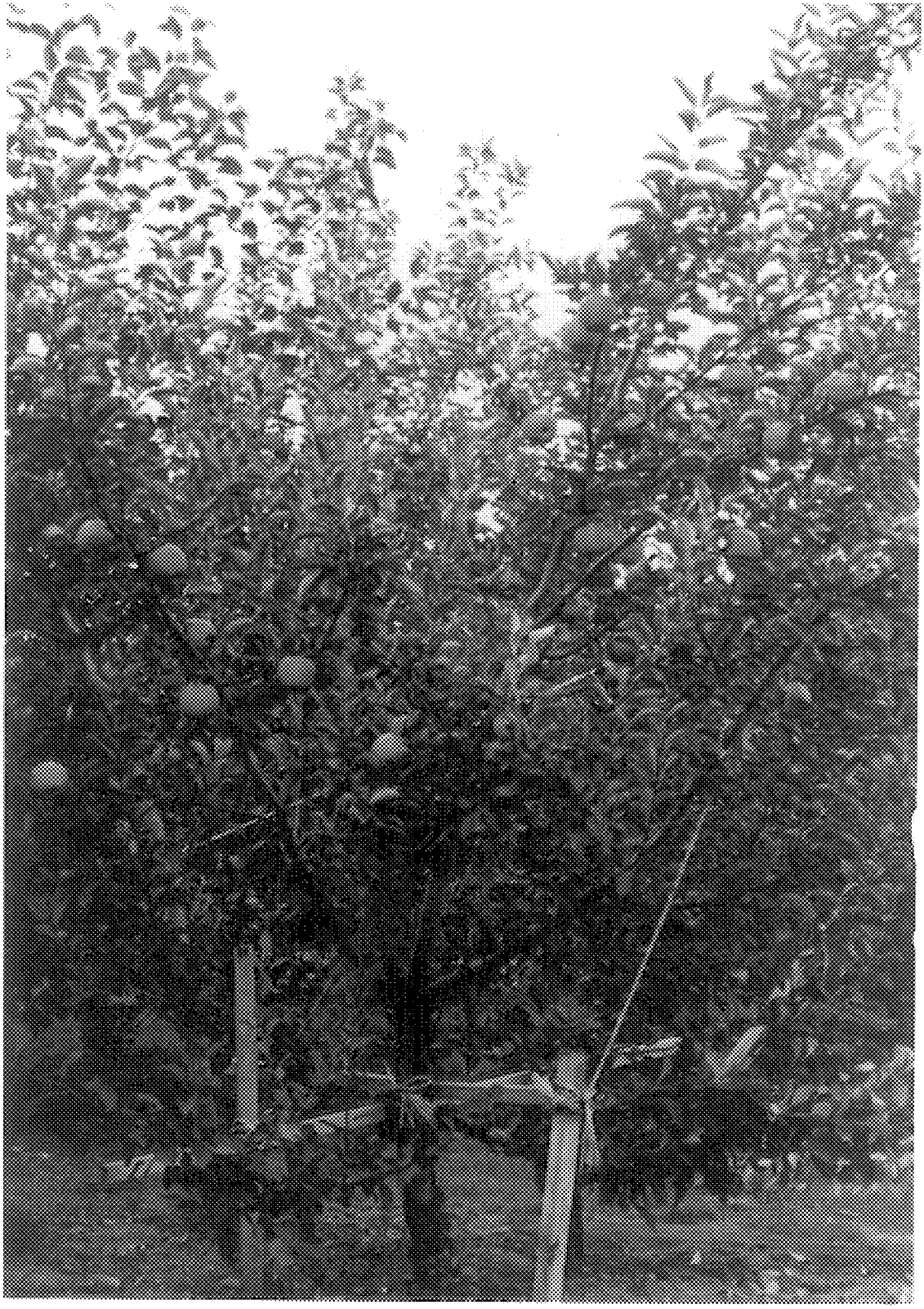
FIG. 3 is a whole plant view.
Figure 4:
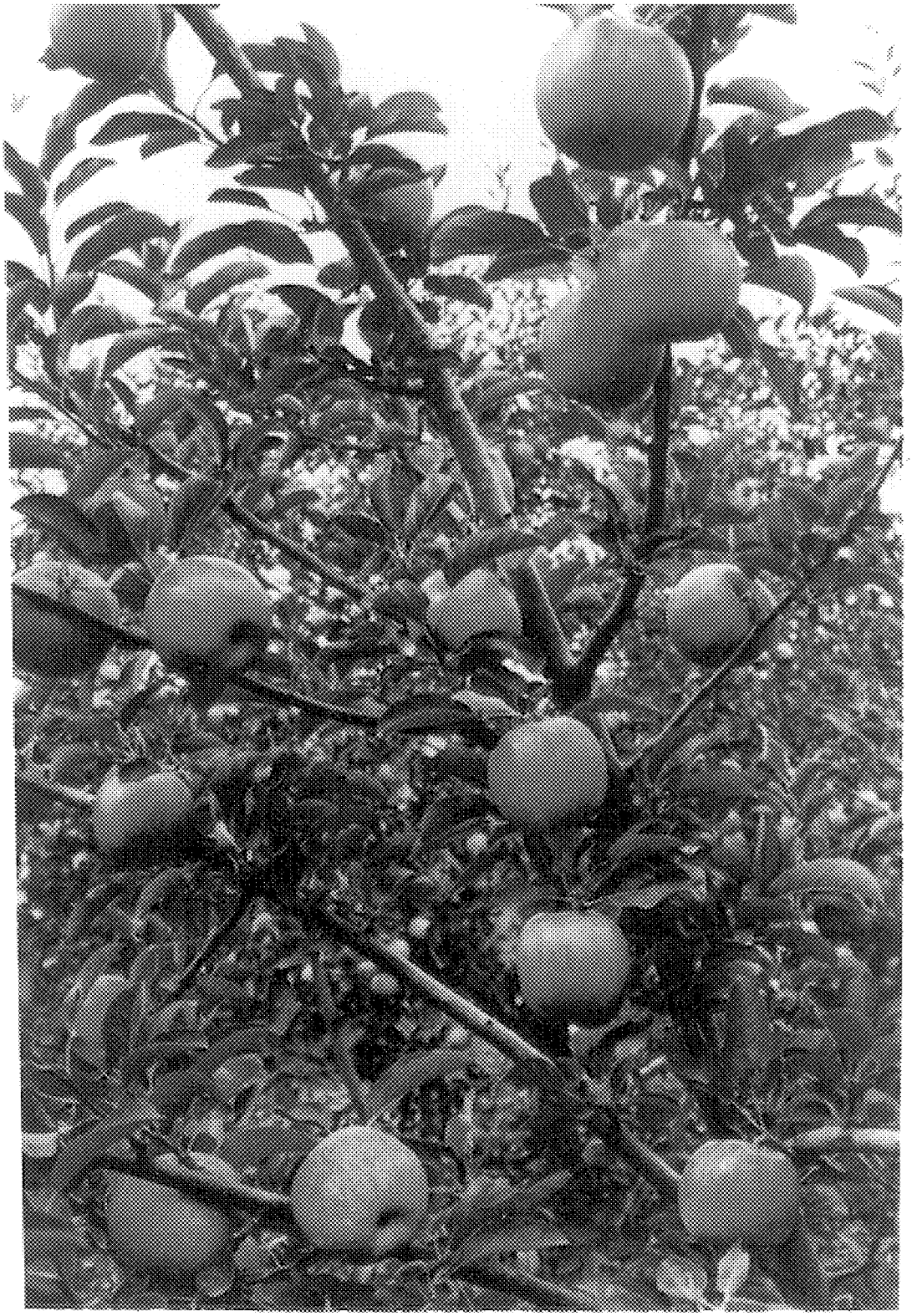
FIG. 4 is a photograph showing typical bearing characteristics of the plant, along with fruit, foliage, and stem coloration of same.
Figure 5:
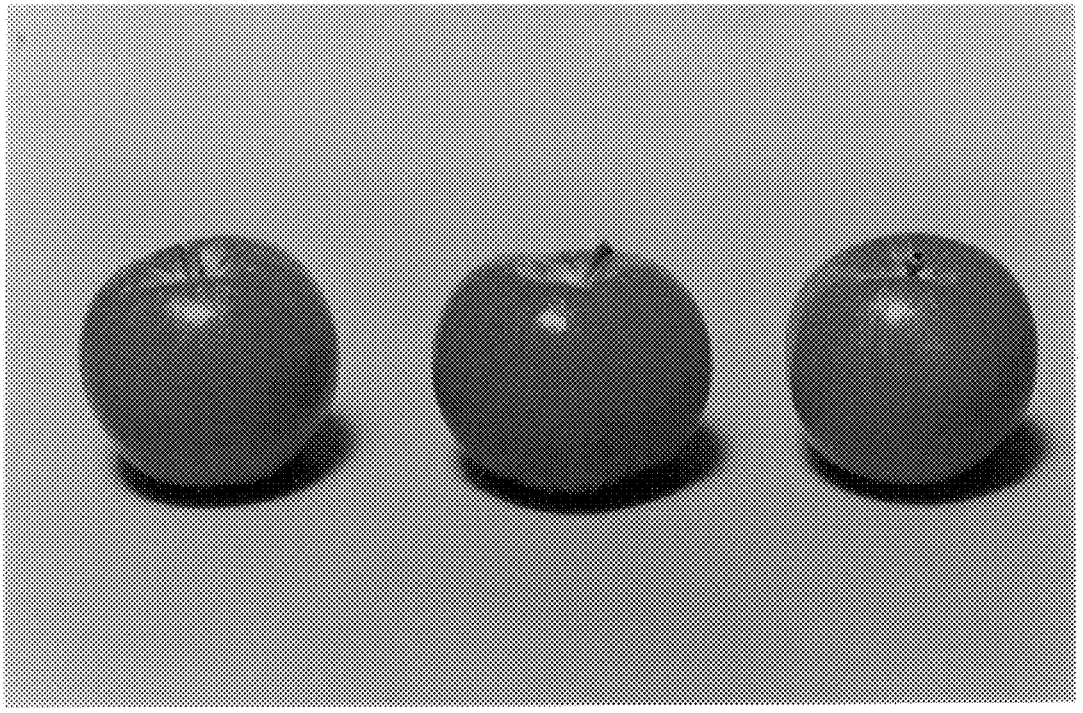
FIG. 5 is a photograph of typical 'MIKI LIFE' fruit.
Figure 6:
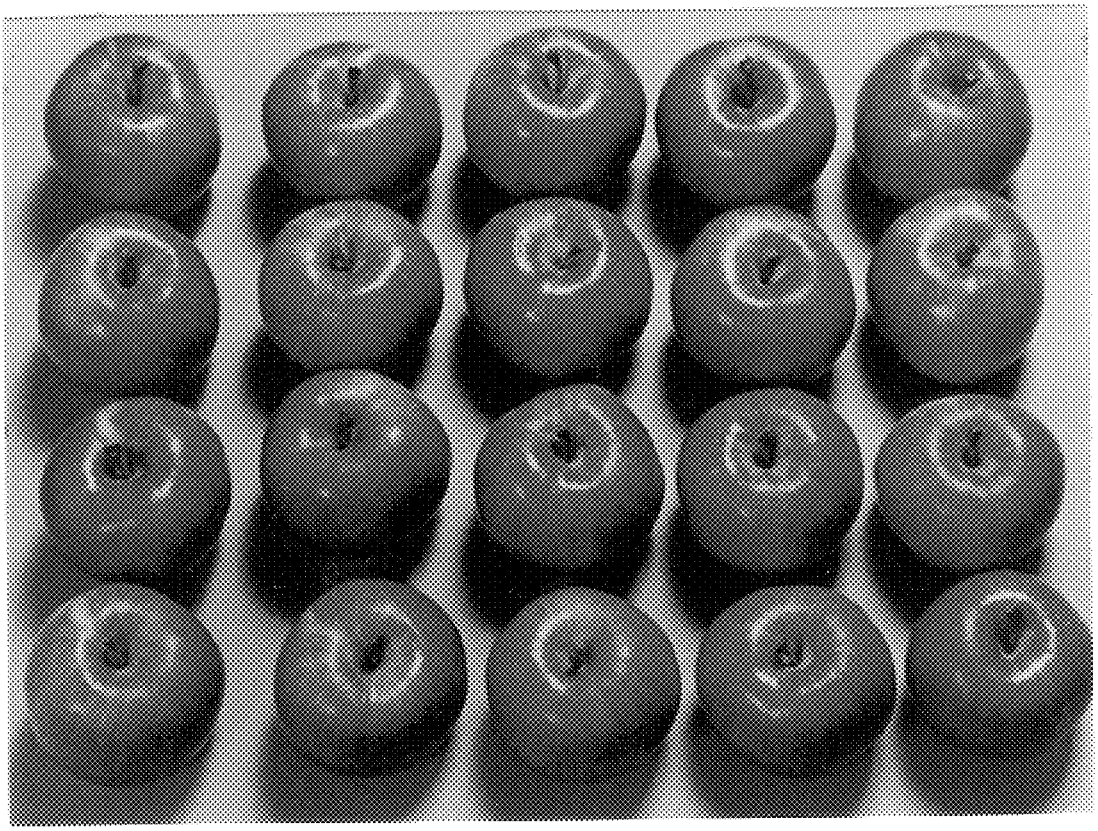
FIG. 6 is a photograph of 'MIKI LIFE' fruit as viewed from the stalk cavity.
Figure 7:
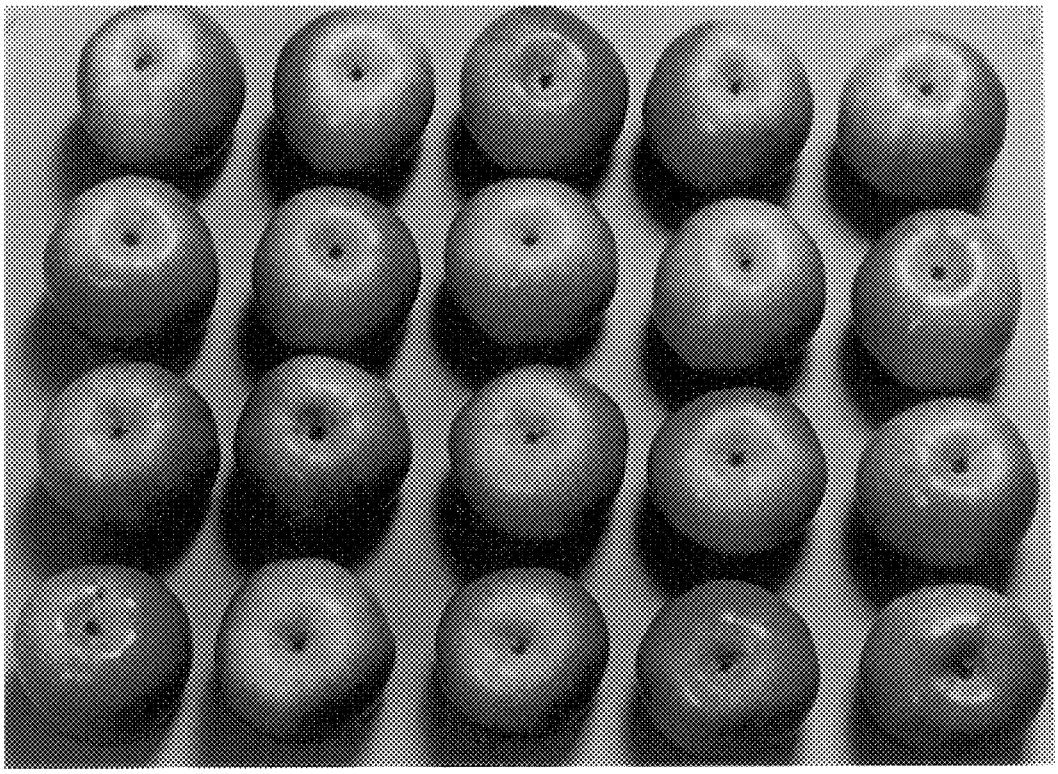
FIG. 7 is a photograph of 'MIKI LIFE' fruit as viewed from the base.
Figure 8:
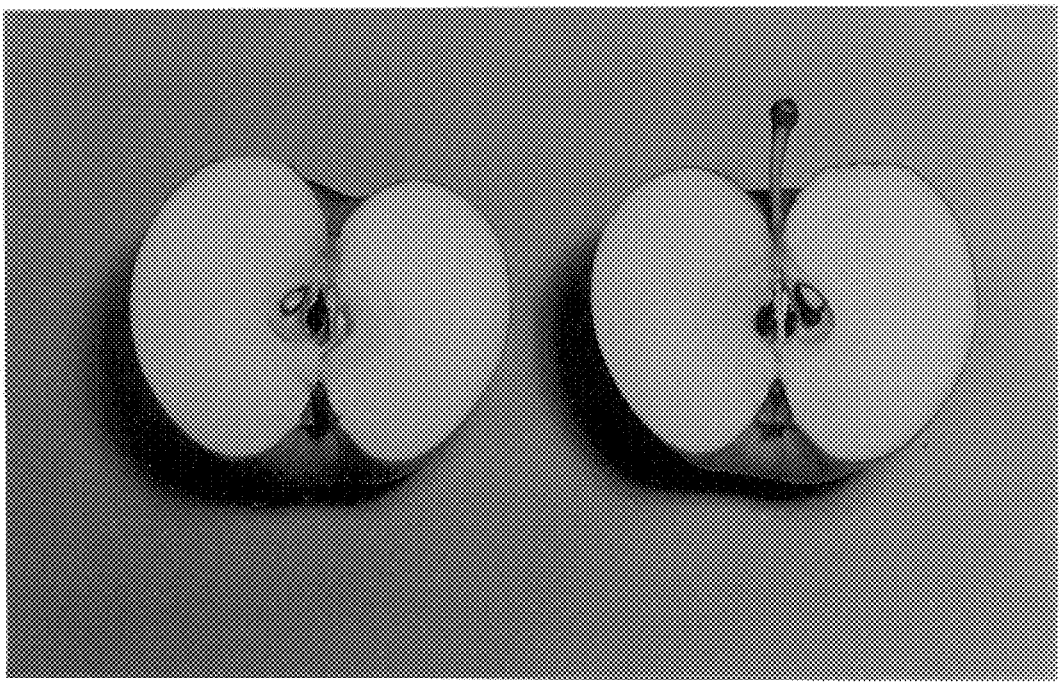
FIG. 8 shows the pedicel, seeds, seed cavity and flesh coloration of the fruit of 'MIKI LIFE'.
Figure 9:
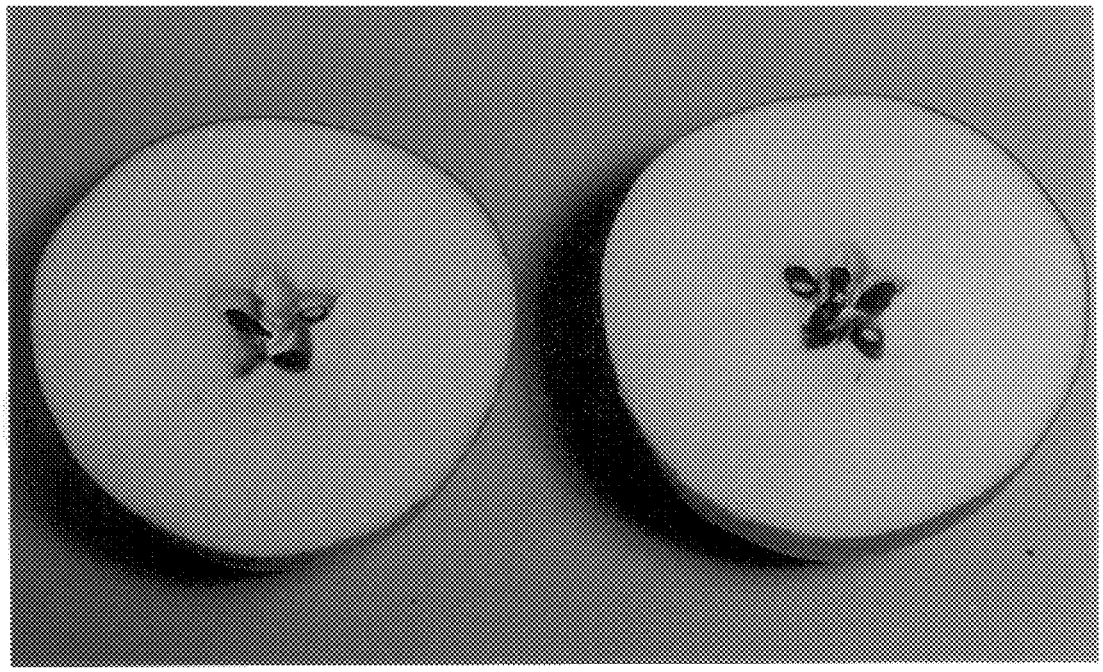
FIG. 9 shows the fruit in cross-section.
Figure 10:
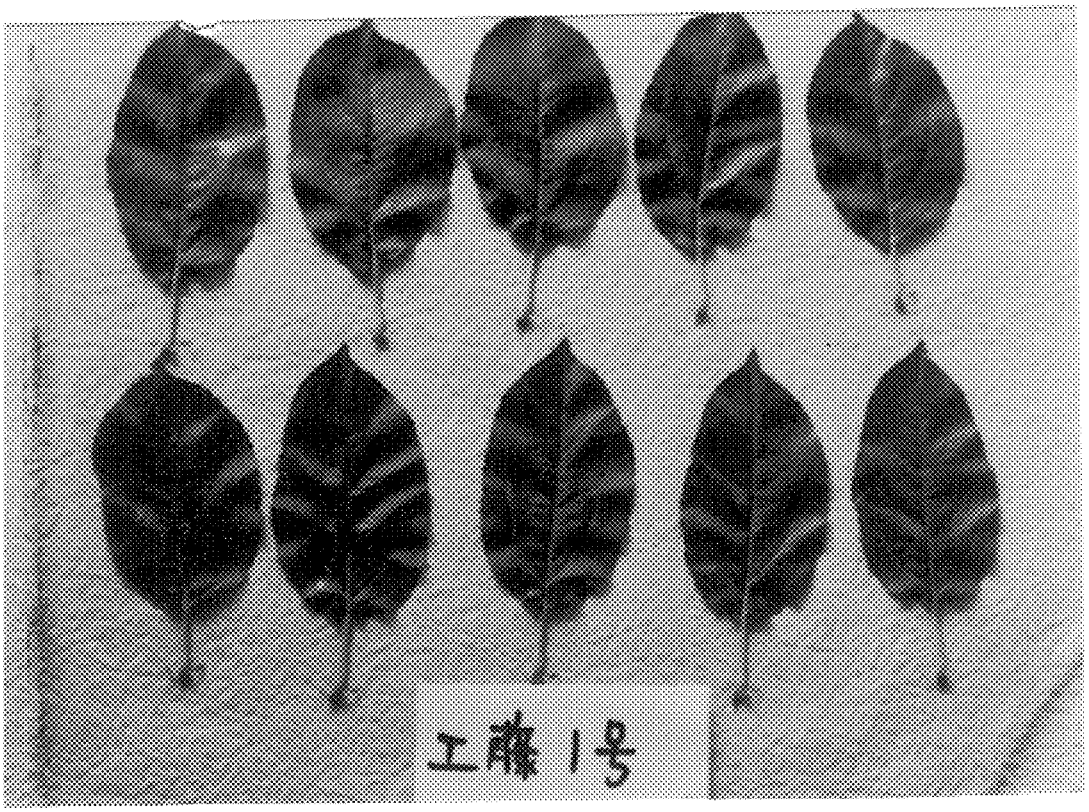
FIG. 10 is a photograph of the foliage, including petiole and stipules.

The characteristics of the new variety 'MIKI LIFE' are as follows, with color description provided according to the Munsell Color Chart.

Botanical name: '*Malus domestica*'.

Tree: The tree is precocious and vigorous, of medium size (smaller than 'FUJI' and about the same size as 'JONATHAN'), with spreading habit similar to 'TSUGARU', and producing many lateral shoots and spurs. The tree is not strong, is intermediate between a spreading style and a straight style, and spreads gradually beyond the central leader. The angle of the branches is of medium width, and fruit is borne on short fruit branches. The color of new treetops is light green. The color of dormant branches is dark reddish brown and lighter than in 'FUJI'. Thinning by cutting more branches than average is necessary to promote growth of a large number of branches because 'MIKI LIFE' tends to have short fruit branches. Picking one fruit in 3.5 to 4 terminal buds is appropriate for obtaining fruit of the disclosed size. Production of lateral flower buds is less than in 'TSUGARU'.

Bark: Dark reddish brown, with relatively high density of medium size (around 1 mm) lenticels which are round in shape and yellow in color.

Shoot: The shoot is of medium thickness and the internode is about 1.7 cm, which is shorter than in 'TSUGARU' cultivated in the same orchard, which has an internode of about 3.0 cm.

Leaves: The leaf is medium size, the length/width ratio of the leaf blade being medium. The leaf margin is wavy with crenate serrations. The length of the leaf blade is about 9.44 cm, the width is about 5.68 cm, the petiole length is about 3.05 cm. The leaf color is dark green (Munsell 7GY2.5/4). The reverse side of the leaf is dull yellow green and is covered with more fuzz than in 'TSUGARU'. The petiole is dull yellow green, with anthocyanin coloring on the reverse side. The stipule is elongated, with a length of about 0.82 cm. Fertilization is desirable for preventing the leaves from turning yellow.

Flower: The flower is of medium size (about 4.04 cm in diameter). The unopened flower is of a strong pink color (Munsell 1R6/12). The flower has five petals of egg shape, and about 20 stamens. The color of the anther is light yellow. The color of the bud is light pink. The time of flowering is midseason, being similar to 'TSUGARU' and 'KANKI'. In the above-mentioned orchard at Aomori, blooming starts around May 9, full bloom is around May 14, with flowers falling around May 18. 'MIKI LIFE' has intermediate self-fertility. The flowers need thinning by picking flowers other than the center flower of terminal buds.

Fruit:

*Shape.*—The fruit is of medium size (around 245 g–280), which is smaller than in 'KANKI'. The shape is round with slight crowning. The ribs are indistinct. The aperture of the eye is medium in size. The base cavity and the stalk cavity are of medium depth and breadth, more shallow and wide than in 'TSUGARU'. The stalk is of medium length (about 2.1 cm), which is longer than in 'TSUGARU', and of medium thickness with distinct swelling at the end.

*Flesh.*—The flesh is yellowish white, very juicy with moderately sweet taste (Brix 13.4) and low acidity (acid 0.294 g/100 ml), good crispness and quality. The flavor is medium and the fragrance intermediate. The firmness is medium, and the texture of the fruit is coarse. Browning is heavy. The mature fruit has no water core.

*Skin.*—The ground color is greenish yellow. The over color (blush) of the skin is bright red (more red than in 'KANKI'), with clear stripes. The skin has medium small lenticels, is moderately shiny, with low greasiness, and is smooth without bloom, and has little rust, if any at all, and little mottling. There is no cracking tendency of the skin.

*Core.*—Conical and small in size, not clear, with five core chambers, a round cross-section and an egg-shaped longitudinal section pointed at the top.

*Calyx.*—Medium in width (wider than in 'TSUGARU'), medium in depth (more shallow than in 'TSUGARU').

*Seed.*—Seeds are numerous and obovate, of medium size.

Harvest season: Early harvesting, around August 28–September 10, which is 10–15 days ahead of 'TSUGARU'. The time between blooming and harvesting is about 118–123 days. Harvesting should be divided into two or three harvests according to the ripening of the fruit.

Storage capacity: Moderate, which is longer than for 'TSUGARU' and is fairly good for an early cultivar. The fruit retains its taste for about one month under normal cold storage. After more than one month of storage the fruit gradually loses firmness and acidity but retains its flavor.

Use: 'MIKI LIFE' is a good variety for dessert apple.

Resistance: 'MIKI LIFE' has intermediate to strong resistance to powdery mildew and Alternaria blotch. It develops very little, if any, core mold. The fruit of 'MIKI LIFE' grown on 'TSUGARU' or 'FUJI' rootstock is about 50 g bigger than the fruit of self-rooted 'MIKI LIFE', but the fruit color and taste are the same.

I claim:

1. A new and distinct variety of apple tree, substantially as illustrated and described herein, bearing early maturing fruit easily coloring in warm weather, having a greenish ground color and bright red overcolor with red stripes, and having a coarse flesh which is very juicy, moderately sweet and with low acidity.

* * * * *